United States Patent [19]

Brunelli et al.

[11] Patent Number: 4,598,208
[45] Date of Patent: Jul. 1, 1986

[54] COLLIMATION SYSTEM FOR ELECTRON ARC THERAPY

[75] Inventors: Richard J. Brunelli; James C. Carter, Jr., both of San Jose, Calif.

[73] Assignee: Varian Associates, Inc., Palo Alto, Calif.

[21] Appl. No.: 742,652

[22] Filed: Jun. 10, 1985

Related U.S. Application Data

[63] Continuation of Ser. No. 659,876, Oct. 15, 1984, abandoned, which is a continuation of Ser. No. 432,606, Oct. 4, 1982, abandoned.

[51] Int. Cl.$^4$ ............................................. G21C 11/00
[52] U.S. Cl. ................................................. 250/515.1
[58] Field of Search ............... 250/492.3, 505.1, 515.1; 378/145, 147

[56] References Cited

U.S. PATENT DOCUMENTS

| | | | |
|---|---|---|---|
| 1,574,884 | 3/1926 | Hendricks | 250/515.1 |
| 2,718,598 | 9/1955 | Graf | 250/515.1 |
| 2,720,708 | 10/1955 | Snell . | |
| 3,466,439 | 3/1966 | Setala . | |
| 3,649,835 | 3/1972 | Brackenbrough et al. | 378/148 |
| 4,140,129 | 2/1979 | Heinz et al. | 250/505.1 |
| 4,221,971 | 9/1980 | Burger | 378/145 |
| 4,266,139 | 5/1981 | Sportelli et al. | 250/515.1 |

FOREIGN PATENT DOCUMENTS

| | | |
|---|---|---|
| 0033050 | 8/1981 | European Pat. Off. . |
| 0037928 | 10/1981 | European Pat. Off. . |
| 0044067 | 1/1982 | European Pat. Off. . |
| 2197299 | 3/1974 | France . |
| 2260977 | 9/1975 | France . |
| 867240 | 5/1961 | United Kingdom . |
| 1083402 | 9/1967 | United Kingdom . |
| 1455038 | 11/1976 | United Kingdom . |
| 1462518 | 1/1977 | United Kingdom . |
| 1597328 | 9/1978 | United Kingdom . |
| 1602144 | 11/1978 | United Kingdom . |

OTHER PUBLICATIONS

Pro. of Symposium on Electron Dosimetry and Arc Therapy, Sep. 10-11, 1981, "Tertiary Collimation of Moving Electron Beams"—Bruce Thomadsen.

Primary Examiner—Bruce C. Anderson
Attorney, Agent, or Firm—Stanley Z. Cole; Keiichi Nishimura; Kenneth L. Warsh

[57] ABSTRACT

An electron collimation system for electron arc therapy treatments consists of a slit collimation system which is movable with the electron beam applicator and is designed to allow for dose compensation in the sagittal direction and a hoop-and-clamp assembly for final field shaping. By correctly designing the shape of the slit in the former and properly adjusting the components of the latter, it is possible to accomplish quite uniform shielding without causing any weight of the shielding material to rest on the patient.

3 Claims, 3 Drawing Figures

COLLIMATION SYSTEM FOR ELECTRON ARC THERAPY

This application is a continuation of application Ser. No. 659,876, filed 10/15/84, abandoned which is a continuation of Ser. No. 432,606 filed 10/4/82 abandoned.

BACKGROUND OF THE INVENTION

This invention relates to an electron collimation system for electron arc therapy treatments and more particularly to the secondary and tertiary collimation devices for rotating electron beams for radiation therapy.

A fixed field collimator which makes use of the conventional jaw-type systems has been disclosed in U.S. Pat. No. 3,767,931, issued Oct. 23, 1973 to Norman H. Williams and assigned to the assignee of the present invention. Such systems, however, are far from adequate as an electron collimation system for electron arc therapy treatments because they are not designed either to allow for dose compensation in the sagittal plane for differing thickness of the patient's body above the target for irradiation nor to provide maximum safety to the patient.

SUMMARY OF THE INVENTION

It is therefore an object of the present invention to provide an electron collimation system for electron arc therapy treatments which is designed to allow for dose compensation.

It is another object of the present invention to provide an electron collimation system for electron arc therapy treatments which is designed for improved patient safety.

The above and other objects of this invention will become apparent from an analysis of the following description of an embodiment.

DETAILED DESCRIPTION OF THE INVENTION

Figure 1:
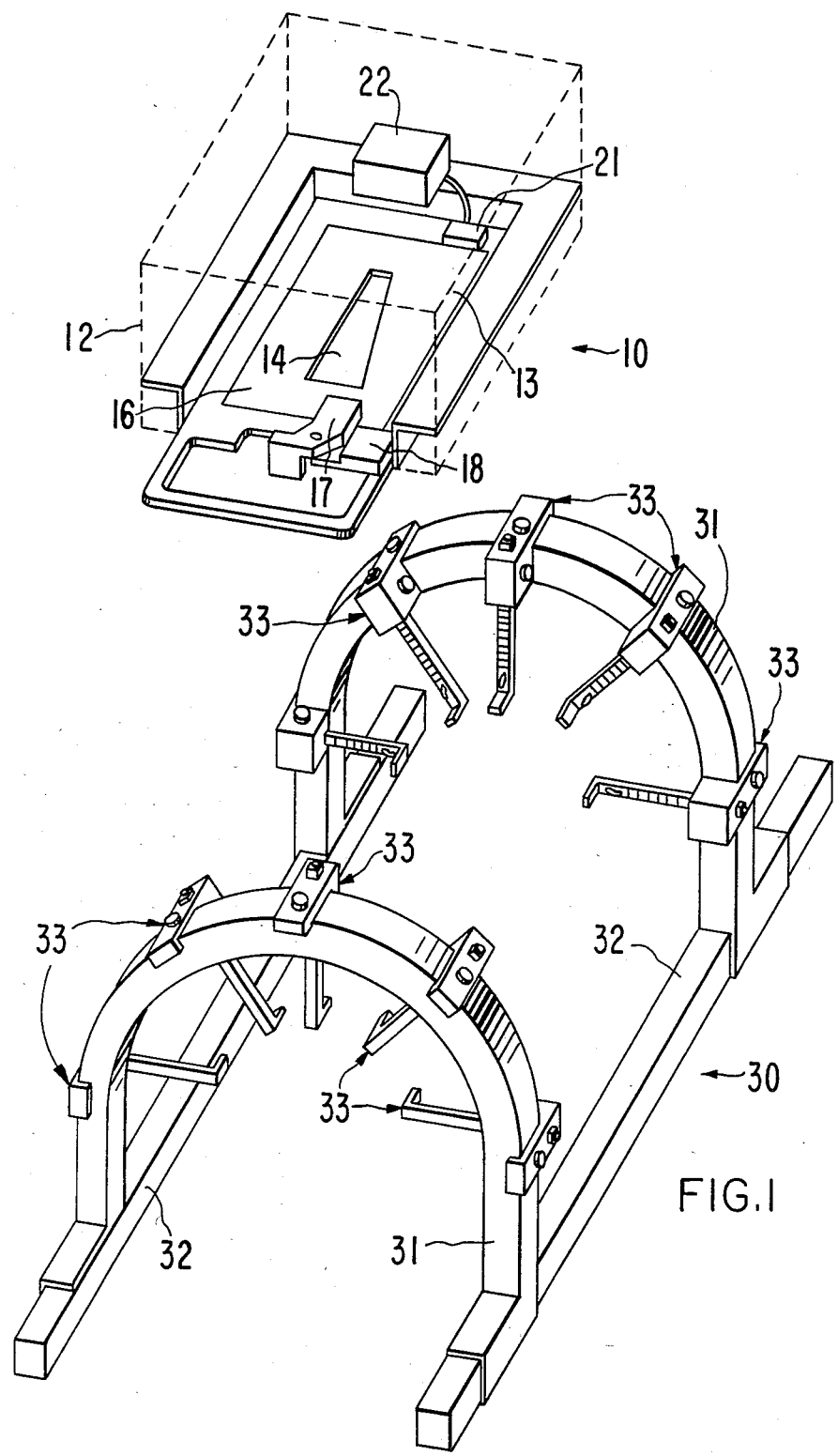
FIG. 1 is a diagonal elevational view of a collimation system for electron arc therapy drawn schematically to show a design for arrangement of its components.

Referring now to FIG. 1, there is shown schematically a design according to which a system of collimation devices according to the present invention may be arranged and used for an electron arc therapy treatment. The system basically consists of two separate parts, a secondary collimation system 10 which is inserted into the electron applicator 12 (shown only schematically in dotted lines) and hence is designed to move with the rotating beam source, and a tertiary collimation system 30 which is set around the therapy patient and remains fixed independent of the applicator motion. Speaking in general terms, the secondary collimation system provides an aperture to confine the beam within an assigned solid angle and to compensate for differing thickness of the patient's body above the target such as a tumor along the length of the patient, while the tertiary collimation system provides a base for locating and holding the final field shaping. The secondary collimation system 10 essentially consists of a shielding mask 13 which provides a specially shaped aperture 14 and a tray 15 for supporting and positioning the mask 13 appropriately and securely with respect to the electron beam applicator 12. For this purpose, tray 15 is provided with a generally rectangular frame 16 into which mask 13 will fit exactly and a latch 17 for securely keeping mask 13 in that position against the rotary motion of the applicator and hence that of tray 15. Latch 17, together with an electrical connector 18, may form a safety-check device for preventing electron arc therapy unless latch 17 is in a proper position. Tray 15 is additionally equipped with a sensor 21 for ascertaining that mask 13 has been properly positioned inside frame 16 and also with an indicator 22 for informing the operator through an electronic coding means that a desired tray carrying a desired mask has been properly inserted into the applicator 12. For the proper functioning of indicator 22, it is presumed that the applicator 12 is provided not only with an accessory slot which is properly shaped and structured to admit and securely hold tray 15 but also with a means for transmitting to the operator the electronically coded information from indicator 22. These sensing and indicating devices on the tray 15 may be connected to the operator's console in such a way that the performance of arc therapy will be automatically prevented unless the intended mask has been appropriately placed in the frame and latched and the tray has been properly inserted into the accessory slot.

Figure 2:
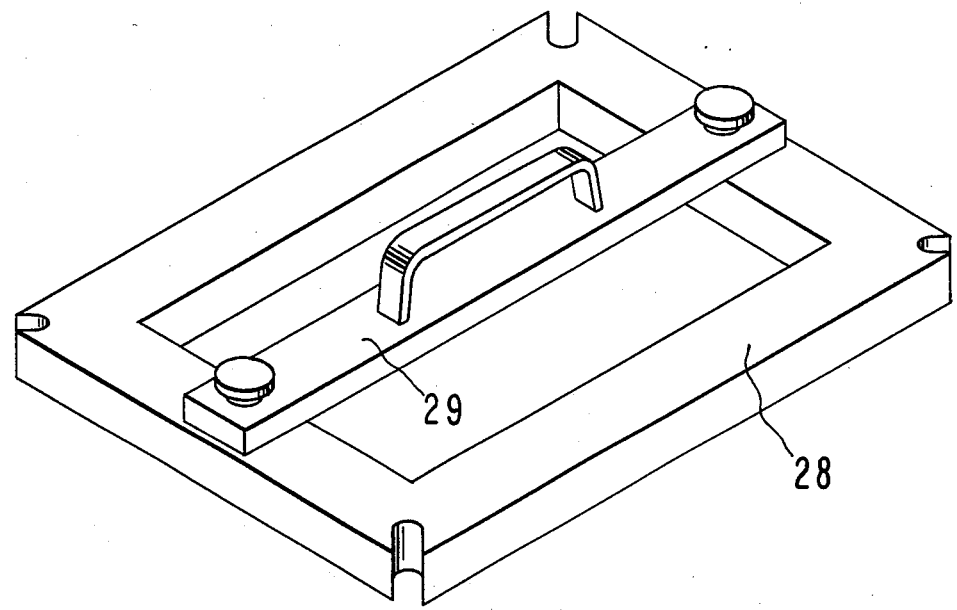
FIG. 2 is a diagonal elevational view drawn schematically of a mold kit which may be used to manufacture shielding masks of the type shown in FIG. 1.
Figure 2:
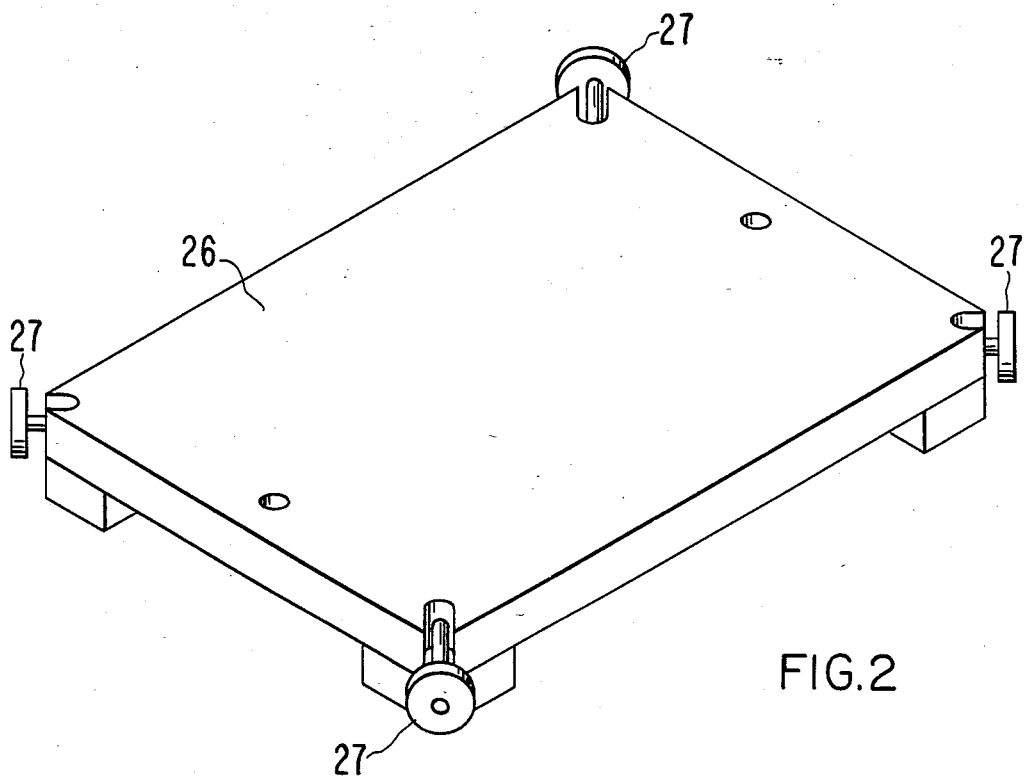

The geometrical shape of aperture 14 depends on the condition of the therapy such as the position of the tumor to be irradiated. It is expected to vary from one case to another; as a practical matter, therefore, it is desirable that the user fabricate his or her own mask. Shown in FIG. 2 is a mold kit which may conveniently be used for such a purpose, consisting of a steel base plate 26 with four toggle clamps 27 and a steel mold frame 28 with a center clamp 29 to hold down the styrofoam pattern (not shown). An alloy with a low melting point such as Lipowitz metal is poured in the styrofoam pattern and a shielding board 13 with a portal of desired shape can be fabricated.

Referring back now to FIG. 1, tertiary collimation system 30 is for the final field shaping and is intended to provide a base for maintaining a shielding plate (not shown) of beam limiting material very close to the patient's skin (preferably no more than a few centimeters). Two substantially semicircular hoops 31 are slidably and detachably mounted on treatment table accessory rails 32 so as to be independently adjustable in the longitudinal direction along the patient's body. Each hoop 31 provides a circumferential mounting surface for five shielding locating clamps 33 over an arc greater than 180°.

Figure 3:
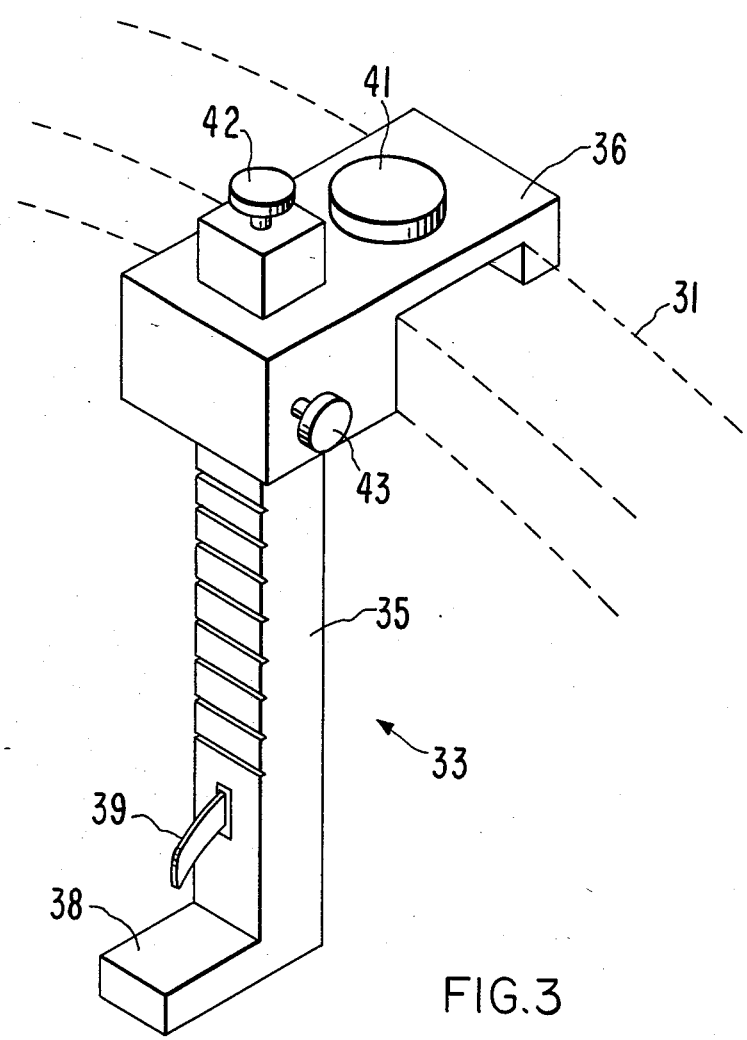
FIG. 3 is an enlarged diagonal elevational view drawn schematically of one of the shielding locating clamps shown in FIG. 1.

Referring next to FIG. 3, there is illustrated more in detail, though only schematically and not true to scale, one of these shielding locating clamps 33. Each clamp 33 consists essentially of a square shaft 35 of which one of the surfaces may be grooved for providing latched and unlatched positions and a block 36 for determining the circumferential position of the clamp 33. For this purpose, block 36 is not only adapted to slide circumferentially along the hoop 31 by using it as a guide-rail, but also provided with the peripheral lock knob 41 for affixing its position with respect to the hoop on which it is made to slide. Block 36 is further provided with a hole through which shaft 35 can move radially with respect to the circular arch of the hoop 31. A rest surface 38 perpendicular to the direction of shaft 35 is provided at the end of shaft 35 near the patient so that a beam limiting material can be placed thereon and clamped by a clamp dog 39 controlled by the radial lock knob 42 at the top of shaft 35. The radial positioning of shaft 35 with respect to block 36 is effected by means of radial indexing knob 43 on a side surface of shaft 35. Radial indexing knob 43 provides for one centimeter incremental positioning of the shielding in the radial direction to within one centimeter of the patient's surface. A rotation by 180° thereof may advance the shaft 35 from one latched position to a next unlatched position or vice versa.

The beam limiting shielding material is to be supplied by the user. It is preferably made of laminates of lead or similar material having a thickness 1.5 mm or less. In view of the total weight to be supported, this is particularly important for treating large arc. By properly spacing the clamps 33 on the hoops 31 and adjusting the shaft positions, it is possible to form the laminates of shielding to maintain a quite uniform shielding to tissue distance and to reduce penumbra effect significantly.

This invention has been described above in terms of but one embodiment. The above description, however, is to be considered as illustrative rather than as limiting, and this invention is accordingly to be broadly construed. First of all, the collimation system described above can be used equally effectively for a variety of radiation treatments other than electron therapy, such as x-ray and gamma ray treatments. Regarding the secondary collimating system, the shielding mask need not be of any particular shape. Any device other than a latch may be used to fasten it to a tray. The mechanism by which the tray is inserted to the applicator and the safety devices described above may be either omitted or replaced by devices of different types. As for the tertiary collimating system, the numbers and shapes of components such as hoops 31, clamps 33, supporting pieces 36, and shafts 35 can be freely changed, depending on the overall design and the purpose for which it is to be used. The scope of the invention is defined by the following claims.

We claim:

1. Apparatus for holding shields in fixed position adjacent a patient positioned on a treatment table for treatment by a radiation therapy beam, said holding apparatus comprising:

two substantially semicircular hoops, each of said hoops having at each of its ends support means for positioning the hoops on guide rails such that the hoops face each other and are adjustable toward and away from each other;

a plurality of mounting blocks adjustably positionable along each of said hoops;

a shaft supported by each said mounting block for adjustable positioning toward and away from the central portion of the hoop with which the respective mounting block is associated; and each said shaft having a rest surface facing outwardly toward its respective block, whereby selective movement of said blocks along said hoops and selective movement of said shafts relative to said blocks enables positioning of said rest surfaces in a variety of different arrangements so as to permit supporting on said rest surfaces variously shaped shields.

2. Apparatus as claimed in claim 1 in combination with arc therapy equipment including a shielding mask positioned outwardly of said hoops.

3. Apparatus as claimed in claim 1 further comprising clamp means located on said shafts outwardly of said rest surfaces for clamping shields on said rest surfaces.

* * * * *